US011859176B2

(12) United States Patent
Chen et al.

(10) Patent No.: US 11,859,176 B2
(45) Date of Patent: Jan. 2, 2024

(54) METHOD FOR IN VITRO ACTIVATION AND/OR EXPANSION OF IMMUNE CELLS

(71) Applicants: Industrial Technology Research Institute, Hsinchu (TW); National Taiwan University Hospital, Taipei (TW)

(72) Inventors: Cheng-Tai Chen, Taoyuan (TW); Chien-An Chen, New Taipei (TW); Wen-Ting Chiang, Hsinchu County (TW); Su-Feng Chiu, Miaoli County (TW); Pei-Shin Jiang, Hsinchu (TW); Jih-Luh Tang, Taipei (TW); Chien-Ting Lin, Taipei (TW); Xuan-Hui Lin, New Taipei (TW)

(73) Assignees: Industrial Technology Research Institute, Hsinchu (TW); National Taiwan University Hospital, Taipei (TW)

( * ) Notice: Subject to any disclaimer, the term of this patent is extended or adjusted under 35 U.S.C. 154(b) by 1241 days.

(21) Appl. No.: 16/228,763

(22) Filed: Dec. 21, 2018

(65) Prior Publication Data

US 2019/0203195 A1 Jul. 4, 2019

Related U.S. Application Data

(60) Provisional application No. 62/609,345, filed on Dec. 22, 2017.

(51) Int. Cl.
| | | |
|---|---|---|
| *C12N 5/00* | (2006.01) | |
| *C12N 13/00* | (2006.01) | |
| *G01N 33/543* | (2006.01) | |
| *C12N 5/0783* | (2010.01) | |
| *C12N 5/078* | (2010.01) | |
| *A61K 9/14* | (2006.01) | |

(52) U.S. Cl.
CPC .......... *C12N 13/00* (2013.01); *C12N 5/0634* (2013.01); *C12N 5/0636* (2013.01); *C12N 5/0646* (2013.01); *G01N 33/54333* (2013.01); *C12N 2501/505* (2013.01); *C12N 2501/515* (2013.01); *C12N 2501/998* (2013.01); *C12N 2529/00* (2013.01); *C12N 2533/10* (2013.01); *C12N 2533/30* (2013.01); *C12N 2535/00* (2013.01); *C12N 2535/10* (2013.01)

(58) Field of Classification Search
None
See application file for complete search history.

(56) References Cited

U.S. PATENT DOCUMENTS

| | | |
|---|---|---|
| 6,352,694 B1 | 3/2002 | June et al. |
| 6,905,874 B2 | 6/2005 | Berenson et al. |
| 7,572,631 B2 | 8/2009 | Berenson et al. |
| 7,749,760 B2 | 7/2010 | Okamura et al. |
| 9,114,100 B2 | 8/2015 | Szabolcs |
| 9,119,807 B2 | 9/2015 | Aarvak et al. |
| 2004/0058445 A1 | 3/2004 | Ledbetter et al. |
| 2009/0017518 A1 | 1/2009 | Wu et al. |
| 2014/0087462 A1 | 3/2014 | Scheffold et al. |
| 2015/0030619 A1 | 1/2015 | Milone et al. |
| 2015/0240204 A1 | 8/2015 | Scheffold et al. |

FOREIGN PATENT DOCUMENTS

| | | |
|---|---|---|
| CN | 104278012 | 1/2015 |
| CN | 104651309 | 5/2015 |
| CN | 105624107 | 6/2016 |
| JP | 2006275600 | 10/2006 |
| JP | 2008164488 | 7/2008 |
| TW | 200903531 | 1/2009 |
| WO | 02072799 | 9/2002 |

OTHER PUBLICATIONS

Kalamasz et al (J. Immunother. 2004, 27(5): 405-418) (Year: 2004).*
Knovel Critical Tables, 2nd Edition, 2008, 1 page (Year: 2008).*
Thomson et al (J. Appl. Polymer Sci. 1996: 2009-2028) (Year: 1996).*
"Search Report of Europe Counterpart Application," dated Mar. 26, 2019, p. 1-p. 7, EP18215030.
James I. Andorko et al., "Designing biomaterials with immunomodulatory properties for tissue engineering and regenerative medicine: Andorko and Jewell," Bioengineering & Translational Medicine, vol. 2 No.2, May 16, 2017, pp. 1-17.
Christine A. Vaine et al., "Tuning Innate Immune Activation by Surface Texturing of Polymer Microparticles: The Role of Shape in Inflammasome Activation," The Journal of Immunology vol. 190 No.7, Feb. 20, 2013, pp. 1-22.
Jiri Kudr et al., "Magnetic Nanoparticles: From Design and Synthesis to Real World Applications," Nanomaterials vol. 7 No. 9 Aug. 29, 2017, pp. 1-29.
Tian Lei et al., "Influence of antigen dose and DC number on CD8+ T cell differentiation and proliferation of OT-I transgenic mice", Journal of Northwest A &F University (Nat .Sci. Ed. ), vol. 37, No. 9, Sep. 10, 2009, with English abstract, pp. 1-6.

(Continued)

*Primary Examiner* — Michael Szperka
*Assistant Examiner* — Marianne DiBrino
(74) *Attorney, Agent, or Firm* — JCIPRNET (57) ABSTRACT

A method for in vitro activation and/or expansion of immune cells is provided, including the steps of: a) providing magnetic particles having multi-protrusive surface modified with at least one type of immuno-inducing substance, in which each magnetic particle includes a copolymer core, a polymer layer, a magnetic substance layer, and a silicon-based layer from the inside to the outside; b) providing a cell solution including at least one type of immune cell in the cell solution; and c) bringing the magnetic particles in contact with the cell solution, in which the at least one type of immuno-inducing substance on the surface of the magnetic particle activates and/or expands the at least one type of immune cell in the cell solution.

16 Claims, 10 Drawing Sheets

(56) References Cited

OTHER PUBLICATIONS

"Office Action of China Counterpart Application", dated Jun. 22, 2022, p. 1-p. 7, P18H39212.

Christine A. Vaine, et al., "Tuning innate immune activation by surface texturing of polymer microparticles: the role of shape in inflammasome activation." J Immunol, vol. 190, No. 1, Apr. 1, 2013, pp. 3525-3532.

Annette Trickett, et al., "T cell stimulation and expansion using anti-CD3/CD28 beads." Journal of Immunological Methods, vol. 275, Apr. 2003, pp. 251-255.

D. Teschner, et al., "In Vitro Stimulation and Expansion of Human Tumour- Reactive CD8+ Cytotoxic T Lymphocytes by Anti-CD3/CD28/CD137 Magnetic Beads." Scandinavian Journal of Immunology, vol. 74, Aug. 2011, pp. 155-164.

Wayne R. Godfrey, et al., "In vitro-expanded human CD4+CD25+ T-regulatory cells can markedly inhibit allogeneic dendritic cell-stimulated MLR cultures." Blood, vol. 104, No. 2, Jul. 15, 2004, pp. 453-461.

Yixin Li et al., "Comparison of anti-CD3 and anti-CD28-coatedbeads with soluble anti-CD3 for expanding human T cells: Differing impact on CD8 T cell phenotype and responsiveness to restimulation, " Journal of Translational Medicine, vol. 8, Issue 104, Oct. 26, 2010, pp. 1-15.

Joel C. Sunshine et al., "Particle shape dependence of CD8+ T cell activation by artificial antigen presenting cells," Biomaterials, vol. 35, Jan. 2014, pp. 269-277.

Karlo Perica et al., "Enrichment and Expansion with Nanoscale Artificial Antigen Presenting Cells for Adoptive Immunotherapy, " ACS Nano., vol. 9, Issue 7, Jul. 2015, pp. 6861-6871.

\* cited by examiner

METHOD FOR IN VITRO ACTIVATION AND/OR EXPANSION OF IMMUNE CELLS

CROSS REFERENCE TO RELATED APPLICATION

This application claims the priority benefit of U.S. provisional application Ser. No. 62/609,345, filed on Dec. 22, 2017. The entirety of the above-mentioned patent application is hereby incorporated by reference herein and made a part of specification.

TECHNICAL FIELD

The disclosure is related to a method for modulating immune cells, and more particularly, to a method for in vitro activation and/or expansion of immune cells.

BACKGROUND

Cancer immunotherapy includes monoclonal antibody drugs, immunological checkpoint inhibitors, cellular immunotherapy, and cancer vaccines, in which significant advances in cellular immunotherapy have attracted considerable attention for cancer immunotherapy.

After the immune cells are purified and separated from the patient's blood, how to efficiently and safely activate and expand the immune cells is a key technique affecting the efficacy of the immune cells. Generally, in the human body, antigen presenting cells (APCs) are used to activate immune cells and trigger an immune reaction to kill foreign substances, among which dendritic cells (DCs) are the most important APCs.

The development of cellular immunotherapy techniques has so far achieved the object of in vitro activation and expansion of immune cells by artificial antigen presenting cells (aAPC). However, the use of genetically engineered feeder cells as aAPC has issues of inconvenience and safety. Therefore, magnetic particles which possess magnetism and may be rapidly separated and modified with specific antibodies as immuno-inducing substances have become the mainstream in the market.

The commercially available magnetic particles currently applied to activate and expand immune cells are almost spherical, and the antibodies for surface modification are also mostly the same. However, the commercially available magnetic particles are mainly applied to activate and expand $\alpha\beta$ T cells, and related products applicable to $\gamma\delta$ T cells are still insufficient. Furthermore, recent research literatures have also pointed out that the size, elasticity, composition of surface antibodies, and modification methods of magnetic particles themselves may affect the performance of activation and expansion of the immune cells thereof.

Therefore, there is an urgent need to develop magnetic particles that may efficiently activate and expand immune cells with a more diverse selection of surface stimulating substances for further application to $\gamma\delta$ T cells.

SUMMARY

The disclosure provides a method for in vitro activation and/or expansion of immune cells that activates and/or expands immune cells with high efficiency.

A method for in vitro activation and/or expansion of immune cells of the disclosure includes the following steps: a) magnetic particles are provided, in which each of the magnetic particles has a surface which is multi-protrusive and modified with at least one type of immuno-inducing substance, and the magnetic particle includes a copolymer core, a polymer layer, a magnetic substance layer, and a silicon-based layer from the inside to the outside; b) a cell solution including at least one type of immune cell is provided; and c) the magnetic particles are brought in contact with the cell solution, and the at least one type of immuno-inducing substance on the surface of the magnetic particle activates and/or expands the at least one type of immune cell in the cell solution.

In an embodiment of the disclosure, the surface of the aforementioned magnetic particle includes a plurality of irregularly shaped protrusions.

In an embodiment of the disclosure, the average height of the aforementioned plurality of protrusions is 100 nm to 5000 nm.

In an embodiment of the disclosure, the average diameter of the aforementioned magnetic particle is 1 µm to 50 µm.

In an embodiment of the disclosure, the aforementioned immune cell includes a T cell, a NK cell, or a combination thereof.

In an embodiment of the disclosure, the aforementioned immune cell includes a regulatory T cell.

In an embodiment of the disclosure, the aforementioned immune cell includes an $\alpha\beta$ T cell, a $\gamma\delta$ T cell, or a combination thereof.

In an embodiment of the disclosure, the aforementioned immune cell includes a $\gamma\delta$ T cell.

In an embodiment of the disclosure, the aforementioned at least one type of immuno-inducing substance may include an anti-CD3 antibody, an anti-CD28 antibody, an anti-TCR $\gamma/\delta$ antibody, an anti-CD83 antibody, an anti-CD137 antibody, a 4-1BBL, an anti-CD2 antibody, an anti-CD335 antibody, or a combination thereof.

In an embodiment of the disclosure, the surface of the aforementioned magnetic particle is modified with the at least one type of immuno-inducing substance through non-covalent binding, covalent binding, avidin-biotin interaction, electrostatic adsorption, hydrophobic adsorption, or a combination thereof.

In an embodiment of the disclosure, the aforementioned copolymer core includes a copolymer formed by copolymerizing a monofunctional monomer and a bifunctional monomer.

In an embodiment of the disclosure, the volume percentage of the aforementioned bifunctional monomer relative to the monofunctional monomer is 0.4% to 2%.

In an embodiment of the disclosure, the aforementioned copolymer core includes a styrene/divinylbenzene copolymer, a methyl methacrylate/triethylene glycol dimethacrylate copolymer, a methyl methacrylate/ethylene glycol dimethacrylate copolymer, a styrene/triethylene glycol dimethacrylate copolymer, a styrene/ethylene glycol dimethacrylate copolymer, or a methyl methacrylate/divinylbenzene copolymer.

In an embodiment of the disclosure, the aforementioned polymer layer includes at least one charged functional group.

In an embodiment of the disclosure, the aforementioned at least one charged functional group includes a carboxyl group, an amine group, or a combination thereof.

In an embodiment of the disclosure, the aforementioned magnetic substance layer includes a paramagnetic substance, a superparamagnetic substance, a ferromagnetic substance, a ferrite magnetic substance, or a combination thereof.

In an embodiment of the disclosure, the aforementioned magnetic substance layer includes an iron ion ($Fe^{2+}$), a cobalt ion ($Co^{2+}$), nickel ion ($Ni^{2+}$), or a combination thereof.

In an embodiment of the disclosure, the thickness of the aforementioned silicon-based layer is at least 1 nm to 50 nm.

Based on the above, compared with the conventional spherical magnetic particles, due to the magnetic particle of an embodiment of the disclosure has multi-protrusive surface, when it encounters with the immune cell that mostly has an irregular appearance, or even dendritic cells with irregular protrusions similar to nerve cells, under the concept of biomimetics, the surface area of the magnetic particle in contact with the immune cell may be increased, thereby improving the effectiveness of the magnetic particles in activating immune cells and/or expanding the number of immune cells.

In addition, in another embodiment of the disclosure, a specific type of immuno-inducing substance may be designed and modified on the surface of the magnetic particles such that the magnetic particles may be applied for the activation and expansion of γδ T cells to overcome the current issue of a lack of related products applicable to γδ T cells. As a result, research and development of techniques in which immune cells are applied, for example, cancer immunotherapy, may be facilitated.

Several exemplary embodiments accompanied with figures are described in detail below to further describe the disclosure in details.

DETAILED DESCRIPTION OF DISCLOSED EMBODIMENTS

Figure 1:
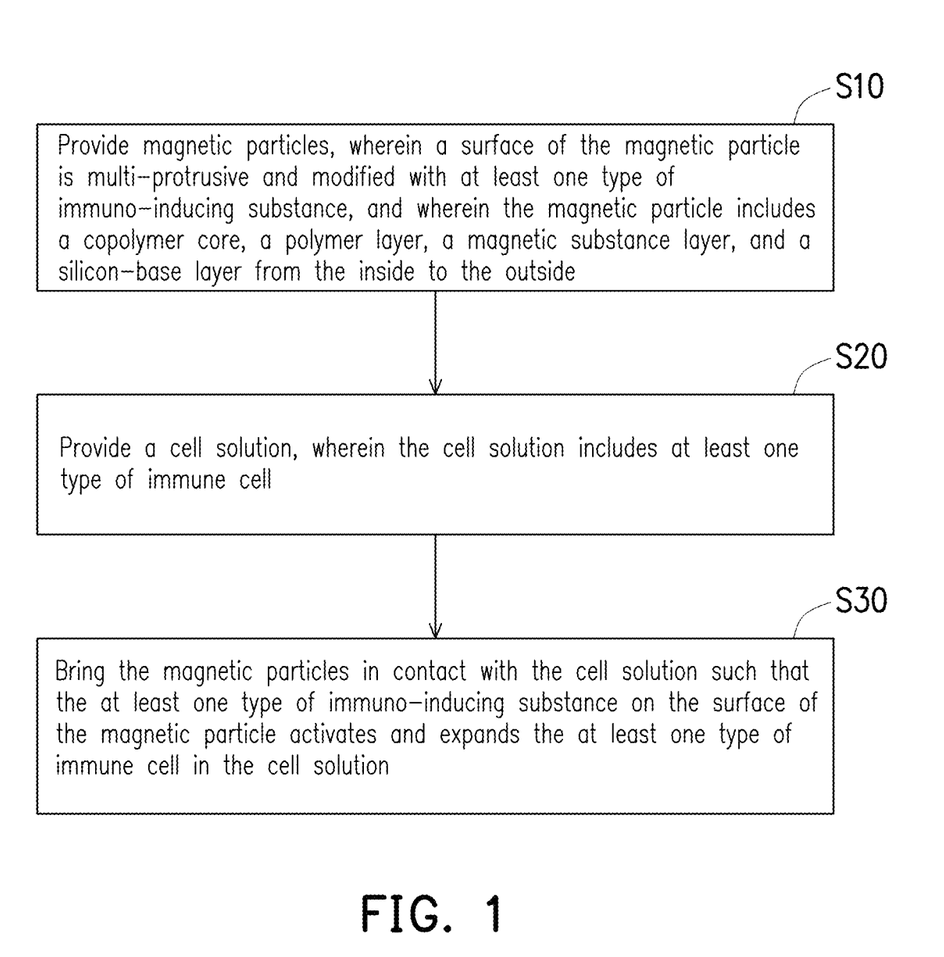
FIG. 1 is a flowchart of a method for in vitro activation and/or expansion of immune cells of an embodiment of the disclosure.
Figure 2:
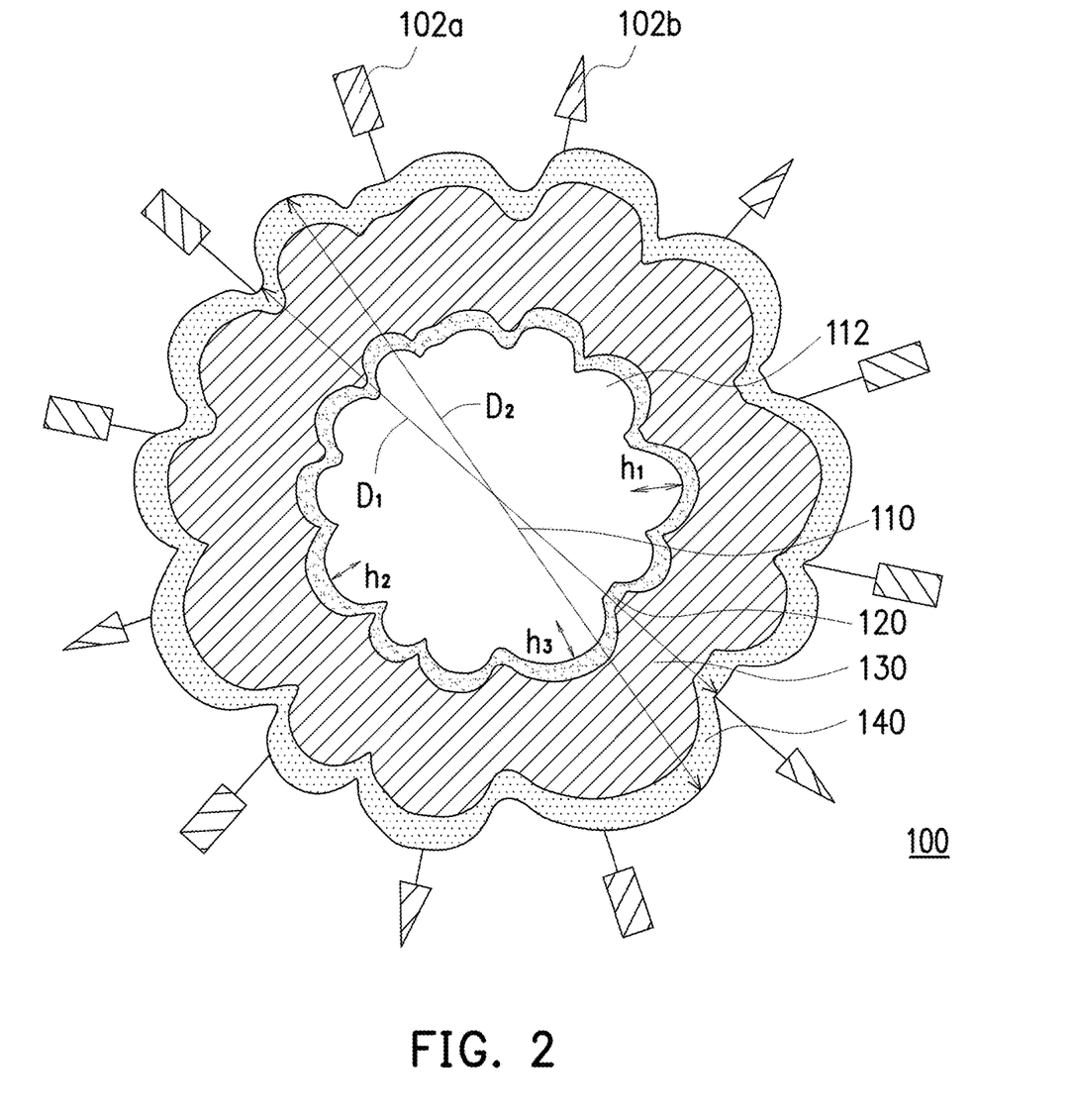
FIG. 2 is a schematic diagram of a magnetic particle for a method for in vitro activation and/or expansion of immune cells of an embodiment of the disclosure.

FIG. 1 is a flowchart of a method for in vitro activation and/or expansion of immune cells of an embodiment of the disclosure. FIG. 2 is a schematic diagram of a magnetic particle for a method for in vitro activation and/or expansion of immune cells of an embodiment of the disclosure. Referring to FIG. 1 and FIG. 2 simultaneously, first, step S10 is performed to provide magnetic particles 100. The surface of the magnetic particle 100 is multi-protrusive and modified with at least one type of immuno-inducing substance 102a and 102b, in which the magnetic particle 100 includes a copolymer core 110, a polymer layer 120, a magnetic substance layer 130, and a silicon-based layer 140 from the inside to the outside. In an embodiment, the magnetic particle 100 has an average diameter D, that is, an average value of the shortest diameter (e.g., $D_1$) and the longest diameter (e.g., $D_2$) of the magnetic particle 100, and may range from 1 μm to 50 μm. In an embodiment, the average diameter of the magnetic particle 100 may be 2 μm to 40 μm. In another embodiment, the average diameter of the magnetic particle 100 may be 3 μm to 30 μm. In yet another embodiment, the average diameter of the magnetic particle 100 may be 4 μm to 20 μm. In still yet another embodiment, the average diameter of the magnetic particle 100 may be 2 μm to 10 μm.

The aforementioned knobby copolymer core 110 is spherical and the surface thereof has a plurality of protrusions 112. An average height h of the protrusions 112, that is, the average value of the vertical distance of the top side of each protrusion 112 to the connection line between two bottom sides of each protrusion 112 (for example, heights $h_1$, $h_2$, and $h_3$), and may range from 100 nm to 5000 nm, such as 100 nm to 500 nm, 500 nm to 1000 nm, 1000 nm to 1500 nm, 1500 nm to 2000 nm, 2000 nm to 2500 nm, 2500 nm to 3000 nm, 3000 nm to 3500 nm, 3500 nm to 4000 nm, 4000 nm to 4500 nm, or 4500 nm to 5000 nm. In an embodiment, an average height h of the protrusions 112 may be 300 nm to 4000 nm. In another embodiment, the average height h of the protrusions 112 may be 500 nm to 3000 nm. In still another embodiment, the average height h of the protrusions 112 may be 800 nm to 2000 nm. In still yet another embodiment, the average height h of the protrusions 112 may be 1000 nm to 1800 nm. In an embodiment, the protrusions 112 may be uniformly or non-uniformly distributed on the surface, and as a whole, the protrusions 112 are substantially irregular protrusions. For example, the protrusions 112 may include, but are not limited to, a papillary shape or a spherical shape.

In an embodiment, the method for forming the aforementioned knobby copolymer core 110 may include, but is not limited to, a dispersion polymerization method, a suspension polymerization method, or an emulsion polymerization method, that is, at least two monomers are polymerized into a copolymer via the above polymerization methods. In an embodiment, the at least two monomers may be lipid-soluble monomers, and may include, for example, monofunctional monomers, bifunctional monomers, or a combination thereof. In an embodiment, in the case of a combination of a monofunctional monomer and a bifunctional monomer, the volume percentage of the bifunctional monomer relative to the monofunctional monomer may be 0.4% to 2%, such as 0.5% to 1.8% or 0.6% to 1.5%.

Further, the monofunctional monomer may be a monovinyl monomer such as styrene, methyl methacrylate, vinyl chloride, or other monofunctional monomers. The bifunctional monomer may be a divinyl monomer such as divinylbenzene, ethylene glycol dimethacrylate, triethylene glycol dimethacrylate, or other bifunctional monomers. In an embodiment, the copolymer may include a styrene/divinylbenzene copolymer, a methyl methacrylate/triethylene glycol dimethacrylate copolymer, a methyl methacrylate/ethylene glycol dimethacrylate copolymer, a styrene/triethylene glycol dimethacrylate copolymer, a styrene/ethylene glycol dimethacrylate copolymer, or a methyl methacrylate/divinylbenzene copolymer, but is not limit thereto.

In an embodiment, the aforementioned polymer layer 120 may cover the knobby copolymer core 110, and the polymer layer 120 includes at least one functional group. In particular, the material of the polymer layer 120 is different from the knobby copolymer core 110, and the functional group may carry a charge, so that the surface of the knobby copolymer core 110 is charged to facilitate the subsequent adsorption of the magnetic substance precursor to form the magnetic substance layer 130. In an embodiment, the functional group may include, but not limited to, carrying a negative charge. Further, the functional group may be a carboxyl group, an amine group, or a combination thereof, but is not limited thereto. It should be mentioned that, although the polymer layer 120 and the knobby copolymer core 110 are depicted as distinguishable layers in FIG. 2, the polymer layer 120 and the knobby copolymer core 110 actually do not exist clear boundaries. Further, in the disclosure, a film layer having a functional group and located on the surface of the knobby copolymer core is collectively referred to as a polymer layer, in practice, however, the polymer layer 120 may be a surface of the knobby copolymer core modified by a functional group, rather than specifically forming a film layer.

The aforementioned magnetic substance layer 130 may cover the polymer layer 120. In an embodiment, the knobby copolymer core 110 covered with the polymer layer 120 may adsorb the magnetic substance precursor to form the magnetic substance layer 130 on the polymer layer 120. In an embodiment, the magnetic substance precursor may include, but is not limited to, an iron ion ($Fe^{2+}$), a cobalt ion ($Co^{2+}$), a nickel ion ($Ni^{2+}$), or a combination thereof. Specifically, the magnetic substance precursor may be a salt of the aforementioned metal ions such as ferrous chloride, cobalt chloride, nickel chloride, or the like. In an embodiment, the surface of the magnetic substance layer 130 may have small protrusions, that is, have a rough surface. Further, the magnetic substance layer 130 may include, but is not limited to, a paramagnetic substance, a superparamagnetic substance, a ferromagnetic substance, a ferrite magnetic substance, or a combination thereof. In an embodiment, the magnetic substance layer 130 may be a ferromagnetic substance. Also, in an embodiment, the magnetic substance layer 130 may have a substantially uniform thickness and entirely cover the copolymer core 110. For example, the thickness of the magnetic substance layer 130 may be 20 nm to 200 nm, and may be, for example, 40 nm to 100 nm.

The aforementioned silicon-based layer 140 may cover the magnetic substance layer 130. In an embodiment, the material of the silicon-based layer 140 may include, but is not limited to, siloxane, silicon glass, silicon oxide, silicate, or a combination thereof. Specifically, the silicon-based layer 140 may include a material such as tetramethoxysilane (TMOS), tetraethoxysilane (TEOS), 3-aminopropyltriethoxysilane (APTES), and 3-glycidoxypropyltrimethoxysilane (GOPTS), or the like. Moreover, in an embodiment, the thickness of the silicon-based layer 140 may be 1 nm to 50 nm, and may be 5 nm to 40 nm, 10 nm to 35 nm, 15 nm to 30 nm, or 10 nm to 20 nm.

In an embodiment, since the polymer layer 120, the magnetic substance layer 130, and the silicon-based layer 140 sequentially formed on the knobby copolymer core 110 do not substantially change the morphology of the knobby copolymer core 110, the resulting magnetic particles 100 still have multi-protrusive appearance. As a result, the surface area of the magnetic particles 100 which may be in contact with the immune cells may be greatly increased. In addition, the multi-protrusive appearance facilitates the close packing of the magnetic particles 100.

In an embodiment, the aforementioned immuno-inducing substances 102a and 102b may be any substance that may elicit immune response, and may include, but are not limited to, a particular type of peptide, protein, or fragment. In an embodiment, a particular type of antibody may be selected as the immune-inducing substances 102a and 102b for a corresponding type of immune cell to be expanded and/or activated. For example, the immuno-inducing substances 102a and 102b may be anti-CD3 antibodies, anti-CD28 antibodies, anti-TCR γ/δ antibodies, anti-CD83 antibodies, anti-CD137 antibodies, 4-1BBL (4-1BB ligand, or CD137 ligand), anti-CD2 antibodies, anti-CD335 antibodies, or a combination thereof. In an embodiment, in order to activate T cells, at least two different antibodies, such as anti-CD3 antibodies and anti-CD28 antibodies, may be selected as the immuno-inducing substances 102a and 102b, but is not limited thereto. It should be noted that although two different types of immuno-inducing substances 102a and 102b are shown in FIG. 2, in other embodiments, the outermost surface of the magnetic particles 100 may include the same type of immuno-inducing substance or two or more different types of immuno-inducing substances. Further, the arrangement of the immuno-inducing substances 102a and 102b in FIG. 2 is merely an exemplification, and is not intended to limit the arrangement of the immuno-inducing substances.

In an embodiment, the immune-inducing substances 102a and 102b may be uniformly distributed on the outermost surface of the magnetic particles 100 to facilitate contacting with the immune cells. In another embodiment, the immuno-inducing substances 102a and 102b may also be modified on the surface of the silicon-based layer 140. The method by which the immuno-inducing substances 102a and 102b are modified to the surface of the magnetic particles 100 may include non-covalent binding, covalent binding, avidin-biotin interaction, electrostatic adsorption, hydrophobic adsorption, or a combination thereof. In addition, other suitable binding methods may also be used. Further, in another embodiment, the immuno-inducing substances 102a and 102b may be modified on the surface of the silicon-based layer 140 by a coupling reagent. The coupling reagent may include, but is not limited to, 3-(3-glycidyloxypropyl)trimethoxysilane, (3-glycidyloxypropyl)triethoxysilane, triethoxysilane-polyethylene-glycol-N-hydroxysuccinimide, or a combination thereof.

Next, referring to FIG. 1 and FIG. 2, step S20 is performed to provide a cell solution, and the cell solution includes at least one type of the immune cell. In an embodiment, the immune cell may include, but is not limited to, an αβ T cell, a γδ T cell, a regulatory T cell, a NK cell, or a combination thereof. In another embodiment, the immune cell is, for example, a γδ T cell.

Thereafter, please continue to refer to FIG. 1 and FIG. 2. Step S30 is performed to bring the magnetic particles 100 in contact with the cell solution such that at least one type of the immuno-inducing substance 102a and 102b on the surface of the magnetic particles 100 may activate and expand the at least one type of the immune cell in the cell solution. In an embodiment, the immune cell is exemplified by a γδ T cell, and the immune-inducing substances 102a and 102b on the surface of the magnetic particles 100 may be anti-TCR γ/δ antibodies and 4-1BBL. In an embodiment, the aforementioned contact may be achieved by mixing approximately equal numbers of the magnetic particles 100 and the immune cells.

The cell expansion ratio of the number of living cells of the aforementioned immune cell varies depending on the cell type, the inter-individual difference, and the culture environment. In terms of the culture environment, the operator may select the desired culture scale according to actual needs. For example, the cell expansion ratio of the number of living immune cells of a small-scale culture environment (for example, a 6-well culture dish) may be 20 to 120, such as 30 to 110, 40 to 100, etc., but is not limited thereto. The cell expansion ratio of the number of living immune cells of a large-scale culture environment (for example, a bioreactor) may be 100 to 8000, such as 500 to 7000, 800 to 6000, etc., but is not limited thereto. In a particular embodiment, the cell expansion ratio of the number of living cells of certain immune cells may even reach tens of thousands. In general, the average expansion ratio of the number of living immune cells may be 20 to 1000. In an embodiment, the average expansion ratio of the number of living immune cells may be 30 to 900. In another embodiment, the average expansion ratio of the number of living immune cells may be 40 to 800.

Further, in an embodiment, the magnetic particles 100 may have residual magnetism, that is, after the applied magnetic field is removed, the magnetic properties of the magnetic particles 100 do not disappear, but tend to stay to some extent. As a result, in an embodiment, when the magnetic particles 100 are dispersed in the cell solution, the magnetic particles 100 may be arranged in a row via the residual magnetism, but are not limited to only a single row, and the chance of contacting with the immune cells by the row(s) of magnetic particles 100 is increased due to the larger overall surface area. Also, in an embodiment, a plurality of rows of the magnetic particles 100 may be aggregated with the immune cells to facilitate the activation and/or expansion of the immune cells.

The aforementioned magnetic particles have multi-protrusive surface similar to the most potent antigen presenting cells (APCs) in the human body, and even similar to dendritic cells (DCs). Therefore, under the concept of biomimetics, it can be speculated that the knobby magnetic particles may be in contact with the immune cells through larger surface area, thereby facilitating the activation and/or expansion of the immune cells.

Specific experimental examples are exemplified below to specifically describe the method for in vitro activation and/or expansion of immune cells.

Figure 3A:
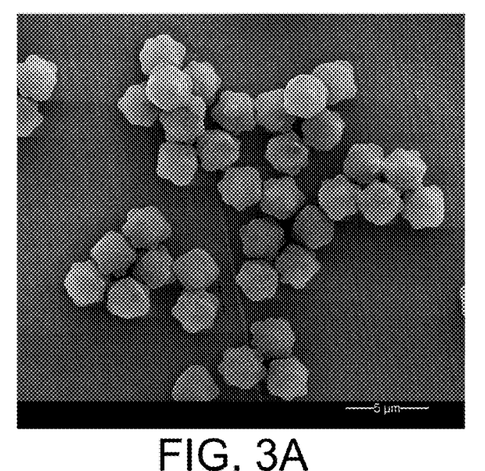
FIG. 3A to FIG. 3C are sequentially electron micrographs of knobby magnetic particles having an average diameter of 2.5 μm, 4.5 μm, and 8.5 μm respectively in experimental example 1 of the disclosure.
Figure 3B:
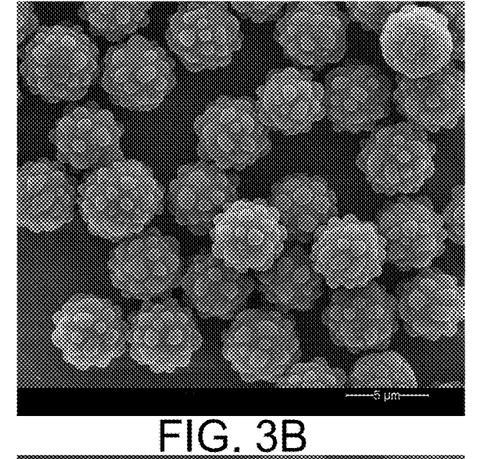
Figure 3C:
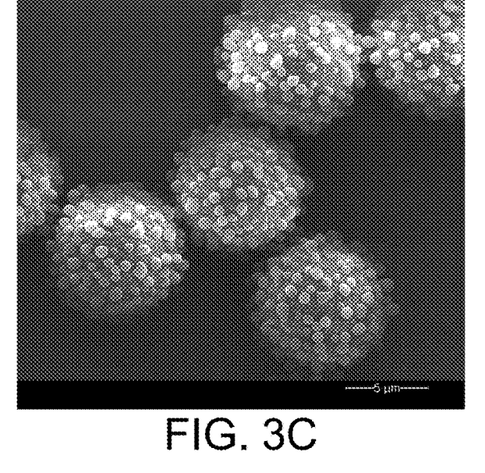
Figure 4:
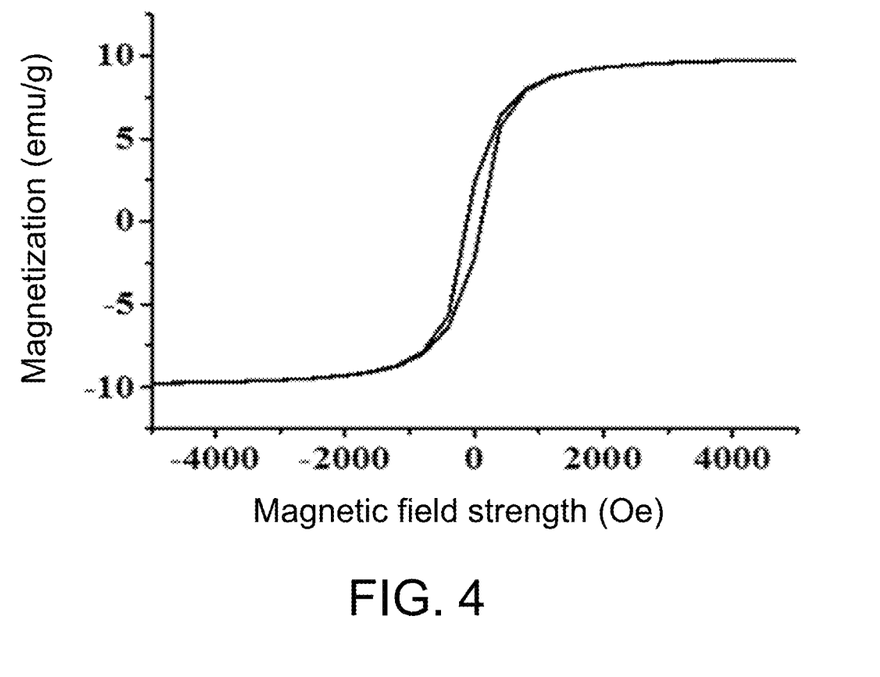
FIG. 4 is a hysteresis curve of the knobby magnetic particles in experimental example 1 of the disclosure.

Experimental Example 1: Modification of an Immuno-Inducing Substance to the Surface of Knobby Magnetic Particles (1) Surface Functionalization of Knobby Magnetic Particles First, three types of knobby magnetic particles of the disclosure were provided, which had an average diameter of 2.5 μm, 4.5 μm, and 8.5 μm, respectively, and the morphologies illustrated by electron microscope (10000×) were as shown in FIG. 3A to FIG. 3C. Further, taking the knobby magnetic particles having an average diameter of 4.5 μm as an example, the hysteresis curve analysis chart thereof is as shown in FIG. 4. Generally, when the magnetic field strength is 0, if the hysteresis curves are coincident and the magnetization is 0, paramagnetism is observed, and if the hysteresis curves do not overlap, ferromagnetism is observed. According to FIG. 4, it can be known that the knobby magnetic particles are ferromagnetic.

1 gram of the knobby magnetic particles, 100 mL of deionized water, 500 mL of ethanol, 30 mL of ammonia ($NH_4OH$), and 0.1 mL of 3-aminopropyltriethoxysilane (APTES) were performed to place into a reactor and stirred for reaction at room temperature for 1 hour. After the reaction was completed, the knobby magnetic particles were collected by a magnet. Next, the reaction solution was removed, and the knobby magnetic particles were cleaned by adding deionized water. After cleaning repeatedly with deionized water three times, knobby magnetic particles having a surface modified with an amine group was obtained.

(2) Method for Modifying with Immuno-Inducing Substances

First, about $7×10^7$ of the aforementioned knobby magnetic particles having a surface modified with an amine group were cleaned three times with 100 μL of 4-morpholineethanesulfonic acid (MES) buffer solution (25 mM, pH 5.0). Next, 20 mg of 1-ethyl-3-(3-dimethylaminopropyl)carbodiimide hydrochloride (EDC), 20 mg of N-hydroxysulfosuccinimide sodium salt (NHS), and 4 mg of polyacrylic acid (PAA, 15 kDa) were dissolved in 400 μL of an MES buffer solution. The mixture was then mixed with the cleaned knobby magnetic particles, and the resulting solution was reacted at room temperature for 30 minutes. After the reaction was completed, the knobby magnetic particles were collected by a magnet.

Next, the reaction solution was removed and the knobby magnetic particles were cleaned three times with 100 μL of MES buffer solution, and then a mixture containing 10 μL of anti-CD3 antibodies (manufacturer: ebioscience), 60 μL of anti-CD28 antibodies (manufacturer: ebioscience), and 130 μL of MES buffer solution were added, and the mixture was subjected to overnight reaction at 4° C. Thereafter, 200 μL of a human serum albumin (HSA, manufacturer: Sigma) solution (10 mg/mL, prepared with MES buffer solution) was added, and an overnight reaction was again performed at 4° C.

After the reaction was completed, the knobby magnetic particles were collected by a magnet. Next, the reaction solution was removed, and the knobby magnetic particles were cleaned three times with a PBS buffer solution containing 0.1% HSA and 2 mM ethylenediaminetetraacetic acid (EDTA) for at least 5 minutes each time, and then the knobby magnetic particles were cleaned three times with a PBS buffer containing 0.1% HSA. Lastly, the knobby magnetic particles modified with immuno-inducing substances were dispersed in 1.75 mL of PBS buffer solution containing 0.1% HSA to obtain a solution, which includes knobby magnetic particles having a surface modified with immuno-inducing substances and has a concentration of $4 \times 10^7$ particles/mL.

Experimental Example 2: Activation and/or Expansion of T Cells by Knobby Magnetic Particles Modified with Immuno-Inducing Substances (1) Separation of T Cells from Blood 10 mL of blood and 0.5 mL of T cell separation reagent (named RosetteSep Human T Cell enrichment cocktail, manufacturer: STEMCELL Technologies Inc.) were mixed in a ratio recommended in the product manual and reacted for 20 minutes. Then, a PBS buffer solution containing 2% fetal bovine serum was added via a pipette and mixed in equal volume to obtain a cell solution. Next, the cell solution was added to a gradient density centrifuge tube containing 15 mL of a T cell separation solution and centrifuged at a speed of 1200 rcf for 20 minutes. Thereafter, the cell supernatant was transferred to a new centrifuge tube and centrifuged at a speed of 300 rcf for 10 minutes. Next, after the supernatant was removed, the cells were reconstituted with 5 mL of a PBS buffer solution containing 2% fetal bovine serum, and 20 mL of a red blood cell lysis solution (named RBC lysis buffer, manufacturer: STEMCELL Technologies Inc.) was added to react at 4° C. for 10 minutes, and then centrifugation was performed at a speed of 300 rcf for 8 minutes. Afterward, the cells were reconstituted with 5 mL of a cell culture medium (RPMI 1640 culture medium containing 10% fetal bovine serum (FBS, manufacturer: BI), manufacturer: Gibco), and centrifugation was performed at a speed of 300 rcf for 8 minutes, and then cell cleaning was performed once. Lastly, the cells were reconstituted using a cell culture medium to obtain a high-purity (such as 90% to 97%) T cell solution.

(2) Stimulation and Culture of T Cells $5 \times 10^5$ of the knobby magnetic particles having a surface modified by the immuno-inducing substances and obtained in experimental example 1 were cleaned three times with 0.2 mL of a cell culture medium, and then the knobby magnetic particles were dispersed in 0.15 mL of the cell culture medium. Next, $5 \times 10^5$ of the T cells obtained in (1) of the aforementioned experimental example 2 were mixed with the knobby magnetic particles dispersed in a culture medium and having a surface modified with immuno-inducing substances, and the total volume was made up to 0.5 mL with the cell culture medium to obtain a T cell solution. At the same time, commercially available spherical magnetic particles (Dynabeads®) and $5 \times 10^5$ of the T cells obtained in (1) of the aforementioned experimental example 2 were mixed to obtain a T cell solution served as a comparison group. Then, the T cell solutions of the experimental group and the comparison group were respectively performed to place into a 24-well culture plate (manufacturer: Corning), in which the T cells were stimulated and cultured in a 37° C. incubator containing 5% carbon dioxide (at this time, it is called day 0 of culture).

Then, 0.5 mL of the cell culture solution was added on day 2 of the culture, and the T cells and the magnetic particles were dispersed using a pipette on day 5 of the culture. Thereafter, the mixture of the T cells and the magnetic particles was transferred to a microtube, and the microtube was placed on a magnetic base to attract the magnetic particles to the wall of the microtube, thus a cell suspension stimulated by the immuno-inducing substances but not containing the magnetic particles was transferred to a new 6-well culture dish (manufacturer: Corning). Next, the total volume and cell concentration of the aforementioned stimulated cell suspension which is free of magnetic particles were measured. After the concentration of the cell solution was adjusted to 0.5 to $1 \times 10^6$ cells/mL, the cell suspension was placed in a new culture dish and returned to a 37° C. incubator containing 5% carbon dioxide to continue the culture.

Thereafter, on day 6 to day 8 of the culture, the following steps were repeated every day: the T cells were uniformly dispersed using a pipette and the total volume and the cell concentration of the cell solution were measured, and after the concentration of the stimulated T cell solution was adjusted to 0.5 to $1 \times 10^6$ cells/mL, the stimulated T cell solution was returned to the incubator to continue the culture. On day 9 to day 12 of the culture, the following steps were repeated every day: the T cells were uniformly dispersed using a pipette, and the total volume and cell concentration of the cell solution were measured, and the average expansion ratio of the T cells on days 9 to 12 was calculated using the cell concentration on day 0 as a reference.

FIGS. 5A to 5D respectively show the cell number on different culture days for T cell activation and/or expansion using commercially available magnetic particles and knobby magnetic particles having an average diameter of 2.5 μm, 4.5 μm, and 8.5 μm, in which the commercially available magnetic particles were served as a comparison group.

Figure 5A:
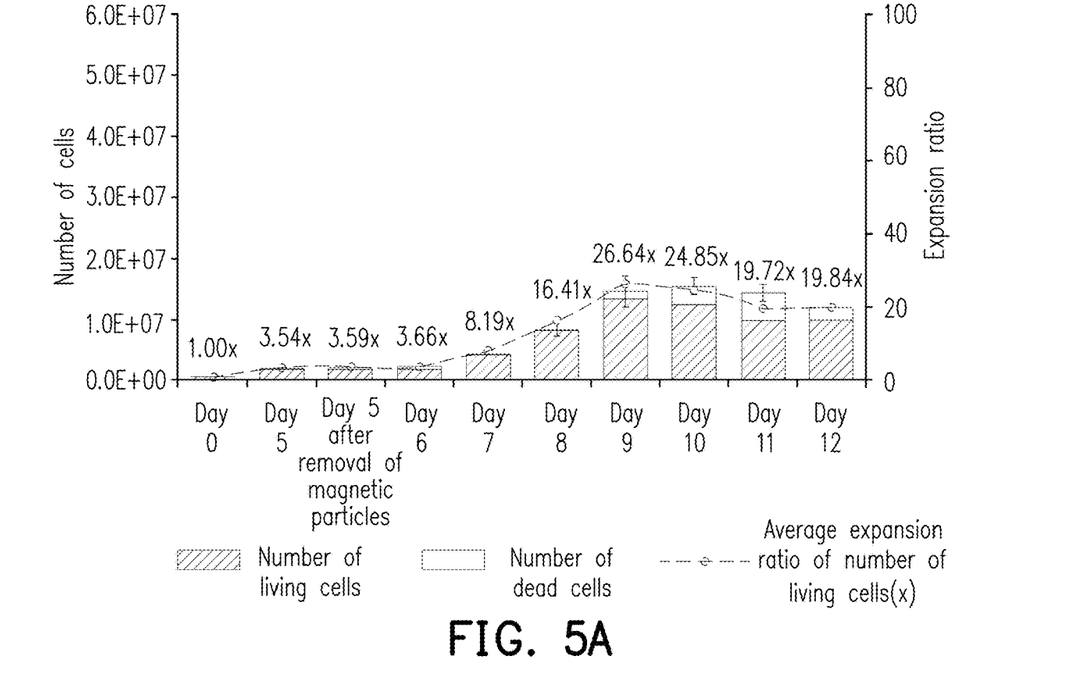
FIGS. 5A to 5D respectively show the cell number on different culture days for T cell activation and/or expansion using commercially available magnetic particles (FIG. 5A) and knobby magnetic particles having an average diameter of 2.5 μm (FIG. 5B), 4.5 μm (FIG. 5C), and 8.5 μm (FIG. 5D), during which the magnetic particles were removed on day 5 of culture. In particular, the horizontal axis represents time (days), the left vertical axis represents the number of cells, and the right vertical axis represents the expansion ratio of cells. In addition, the number of living cells and the number of dead cells are respectively represented by oblique lines and blanks in each bar graph. Otherwise, based on the initial number of cells on day 0 as a control reference, the number of living cells on each of the remaining days was respectively divided by the initial number of cells on day 0 to obtain the average expansion ratio of the number of living cells per day, and the average expansion ratio of the number of living cells calculated on each day was linked by a dotted line to show the expansion trend of the number of living cells during the culture from the day 0 to day 12.
Figure 5B:
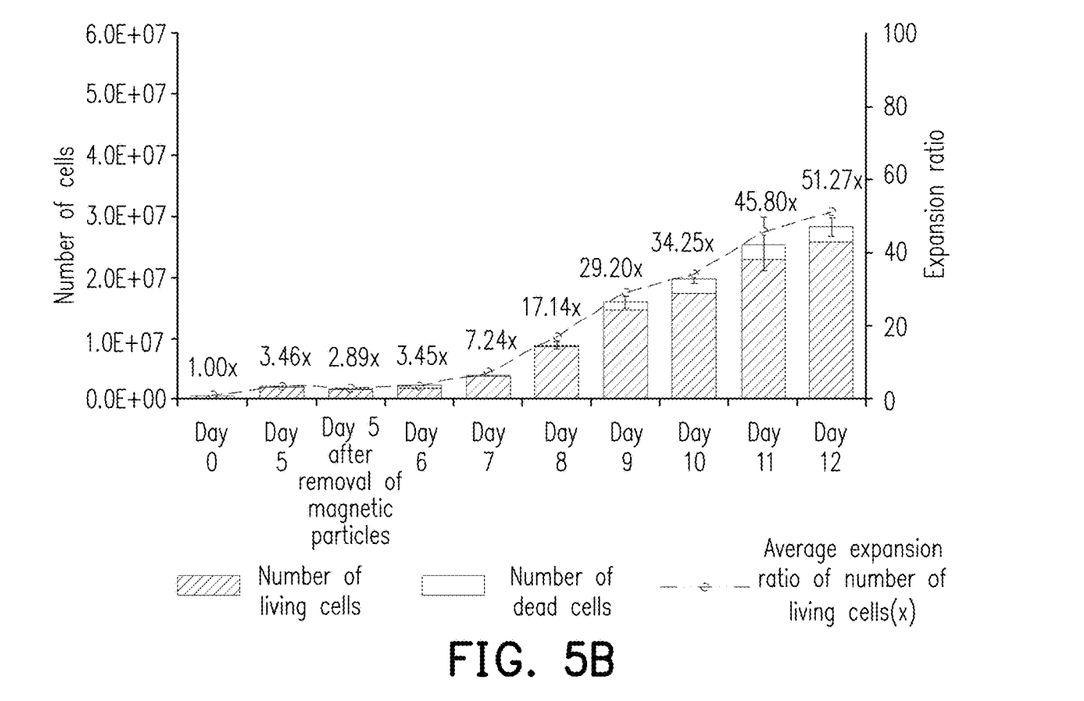
Figure 5C:
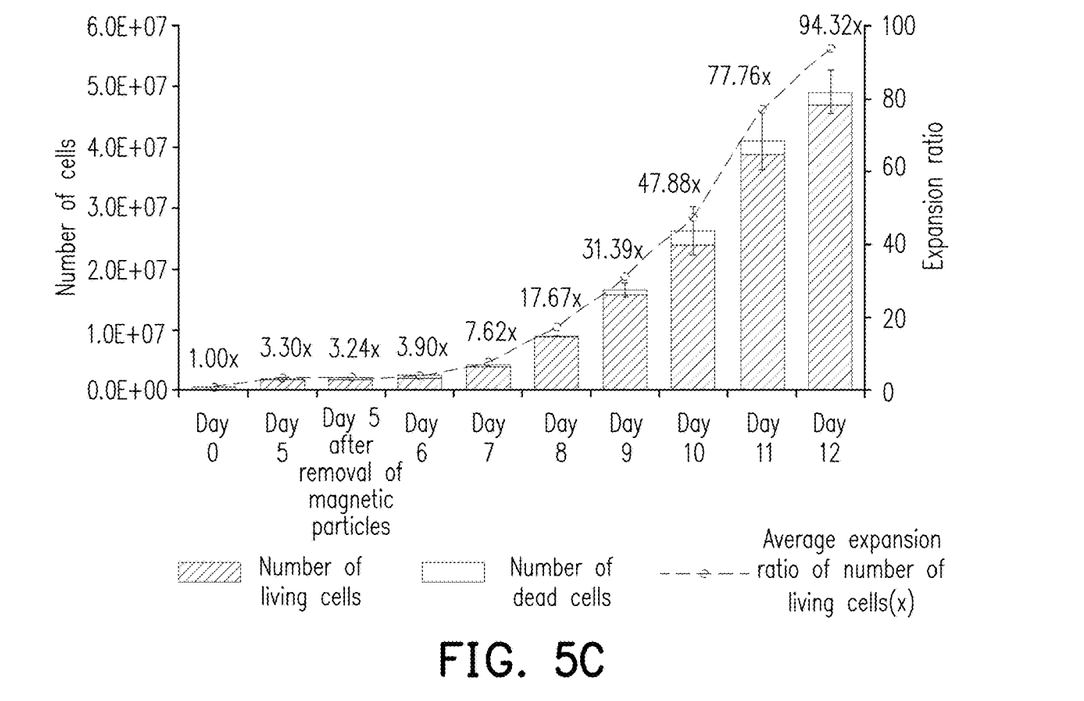
Figure 5D:
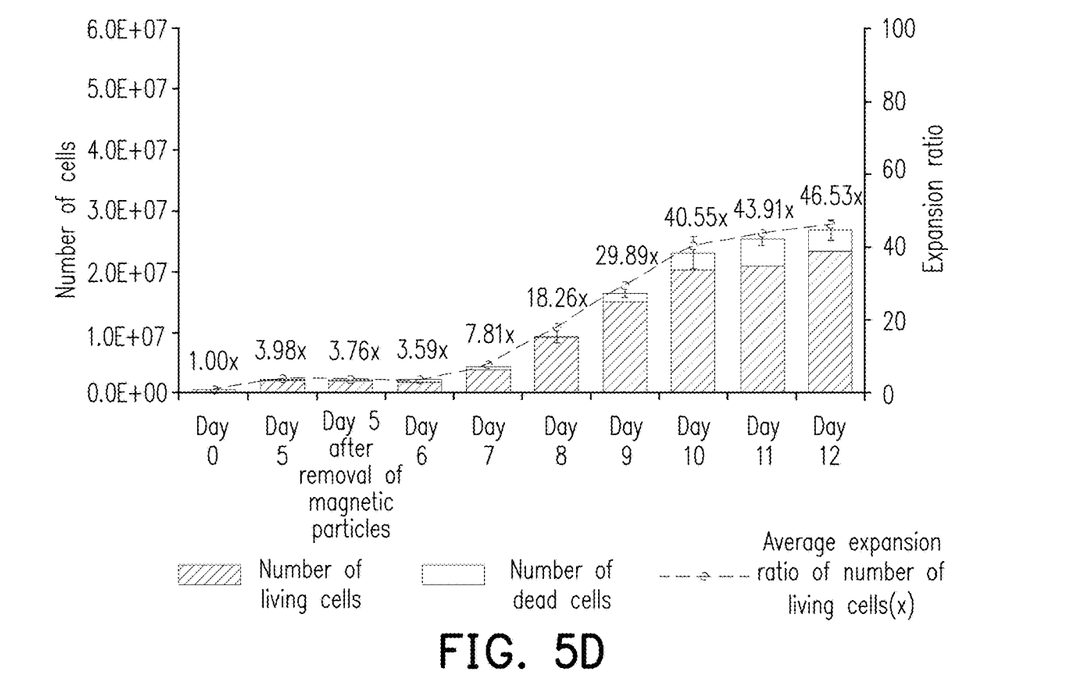

According to the results shown in FIG. 5A to FIG. 5D, on day 9, compared to the average expansion ratio of 26.64 of the T cells of the comparison group, the average expansion ratios of the T cells of the experimental group treated with the knobby magnetic particles having an average diameter of 2.5 μm, 4.5 μm, and 8.5 μm were 29.20, 31.39, and 29.89, respectively. In addition, after day 9, the average expansion ratio of the T cells of the comparison group was gradually decreased or tended to be gentle, but the average expansion ratio of the T cells of the experimental group continued to increase, in which the expansion efficiency achieved by the 4.5 µm magnetic particles (that is, as shown in FIG. 5C) was the most remarkable, reaching an expansion ratio of 90 or more.

Experimental Example 3: Activation and/or Expansion of T Cells by the Knobby Magnetic Particles Modified with Two Antibodies in Different Ratios The operation procedure in experimental example 3 was the same as that of experimental example 2, and the main difference was that in experimental example 3, the magnetic particles of 4.5 µm were used as a test object, and in the modification ratio of the immuno-inducing substance, anti-CD3 antibodies and anti-CD28 antibodies were prepared as antibody mixtures at ratios of 1:2, 1:6, and 1:10, and the antibody mixtures were used to modify the aforementioned 4.5 µm magnetic particles, respectively. In the present experimental example, commercially available spherical magnetic particles (Dynabeads®) were simultaneously served as a comparison group, but the ratio of antibodies on the commercially available spherical magnetic particles could not be confirmed.

Figure 6A:
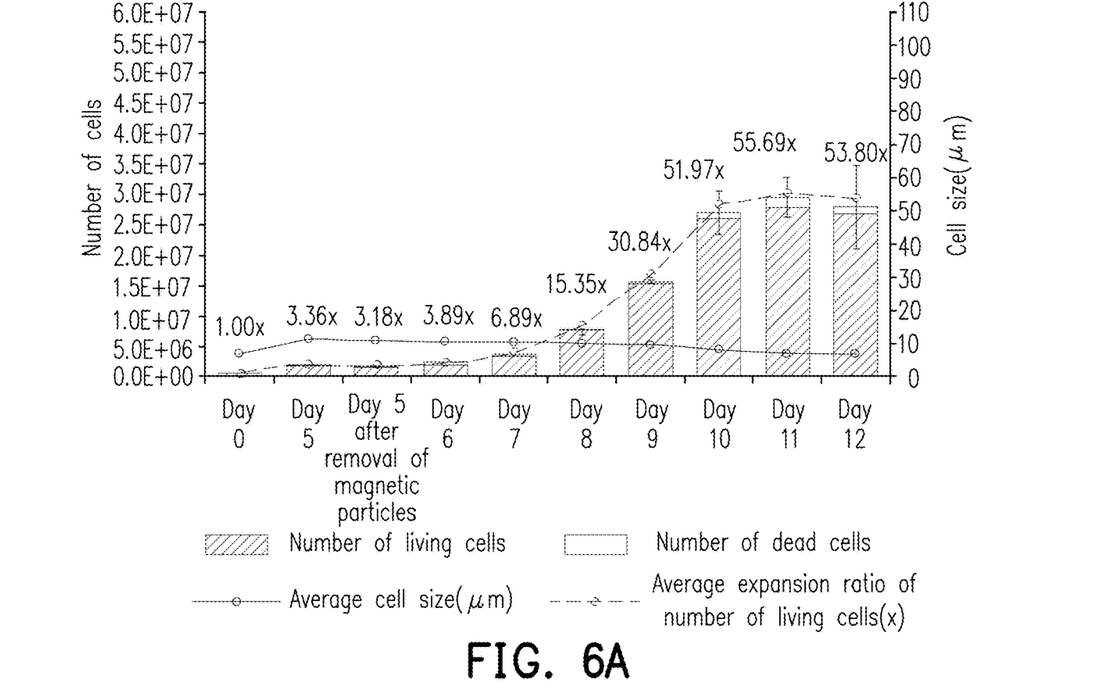
FIGS. 6A to 6D respectively show the cell number on different culture days for T cell activation and/or expansion using commercially available magnetic particles (FIG. 6A) and knobby magnetic particles having a surface modified with antibodies in which the ratios of anti-CD3 antibody to anti-CD28 antibody are 1:2 (FIG. 6B), 1:6 (FIG. 6C), and 1:10 (FIG. 6D), during which the magnetic particles were removed on day 5 of culture. In particular, the horizontal axis represents time (days), the left vertical axis represents the number of cells, and the right vertical axis represents the cell size (μm). In addition, the number of living cells and the number of dead cells are respectively represented by oblique lines and blanks in each bar graph. Otherwise, based on the initial number of cells on day 0 as a control reference, the number of living cells on each of the remaining days was respectively divided by the initial number of cells on day 0 to obtain the average expansion ratio of the number of living cells per day, and the average expansion ratio of the number of living cells calculated on each day was linked by a dotted line to show the expansion trend of the number of living cells during the culture from the day 0 to day 12. Further, the changes of average cell size (μm) during the culture from day 0 to day 12 are shown by a solid line.
Figure 6B:
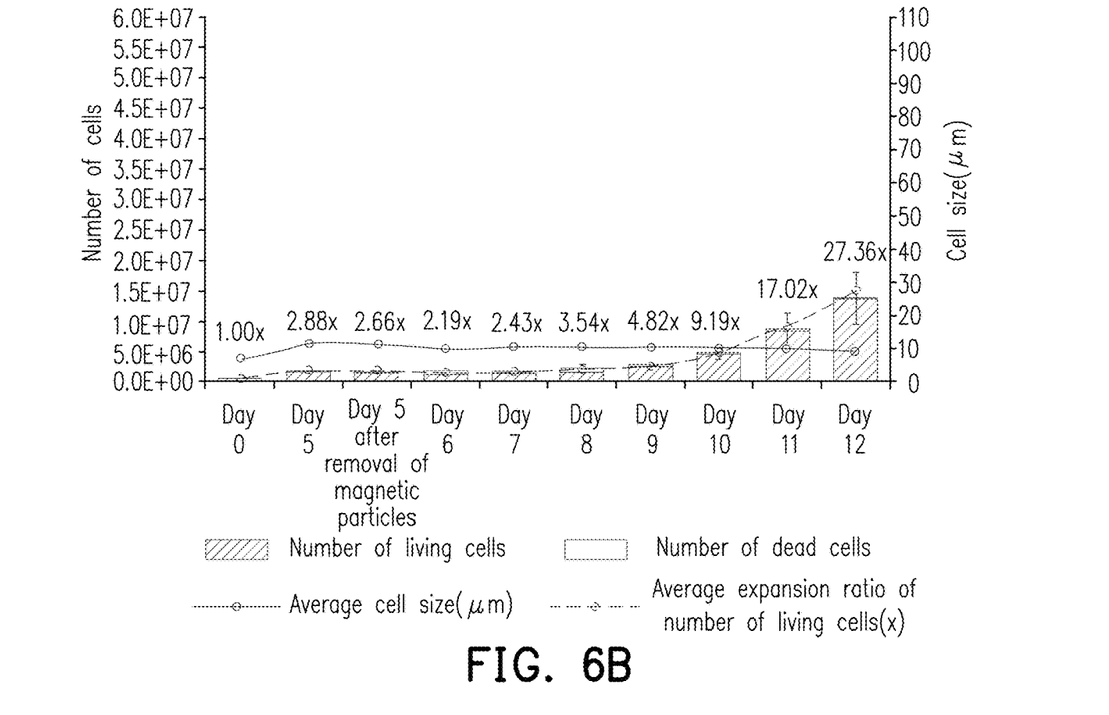
Figure 6C:
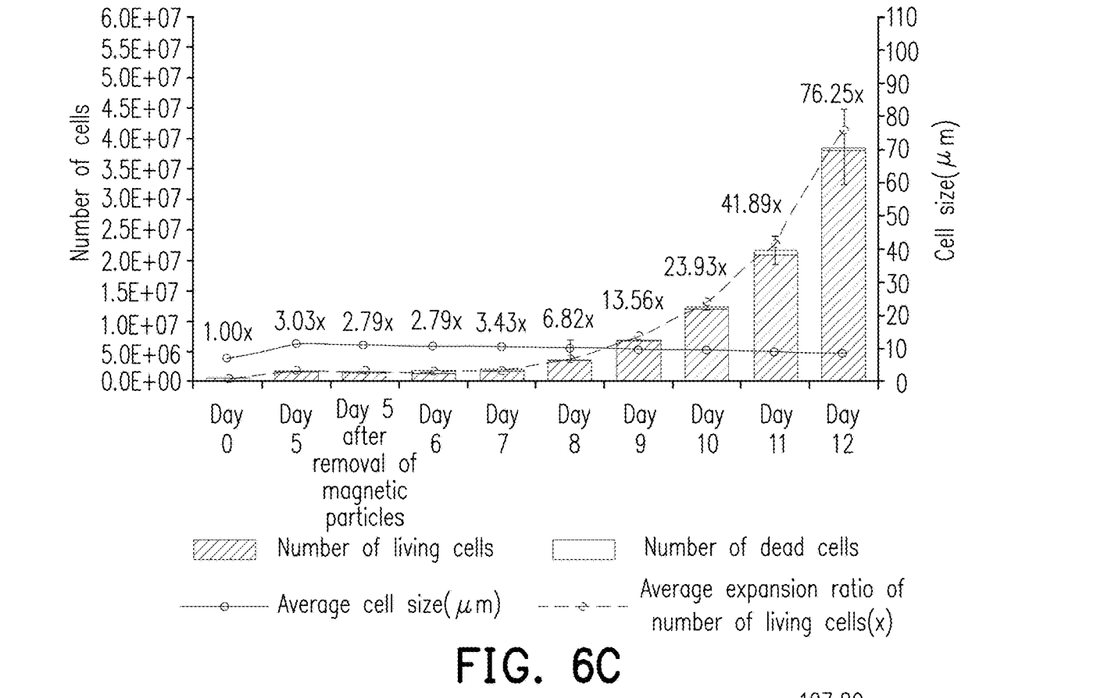
Figure 6D:
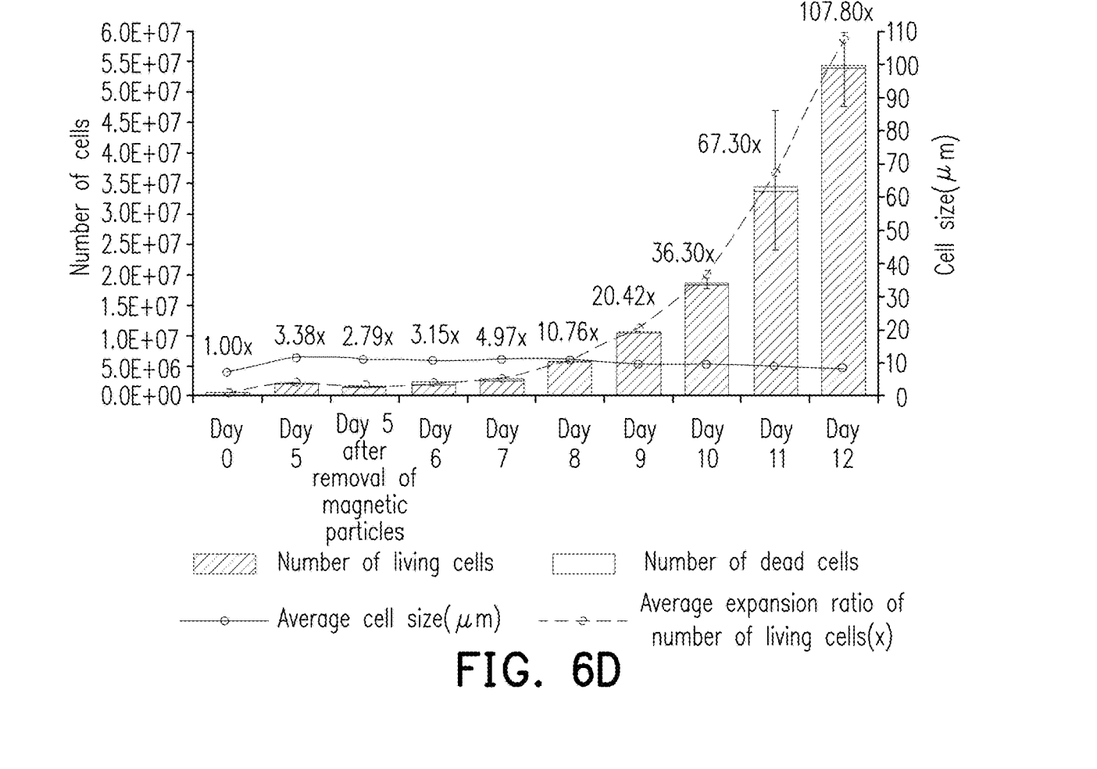

FIGS. 6A to 6D respectively show the cell number on different culture days for T cell activation and/or expansion using commercially available magnetic particles (Dynabeads®) and knobby magnetic particles for which the surface was modified with the antibodies in which the ratios of anti-CD3 antibodies and anti-CD28 antibodies were respectively 1:2, 1:6, and 1:10. According to FIG. 6A to FIG. 6D, it can be known that, compared to the comparison group (FIG. 6A, Dynabeads®), the magnetic particles of the experimental group with surface modified by different ratios of antibodies (FIG. 6B, anti-CD3 antibodies: anti-CD28 antibodies=1:2; FIG. 6C, anti-CD3 antibodies: anti-CD28 antibodies=1:6; FIG. 6C, anti-CD3 antibodies: anti-CD28 antibodies=1:10) all may effectively activate and/or expand the T cells.

Experimental Example 4: Characteristic Analysis of Activated and/or Expanded T Cells Characteristic analysis was performed on the aforementioned T cells of the disclosure activated and/or expanded by the knobby magnetic particles by flow cytometer (SONY SA3800), and the results were simultaneously compared with that of T cells (the comparison group 1 and the comparison group 2) activated and/or expanded by two commercial products (including magnetic particles and modified antibodies, in which the products only disclose that the modified antibodies thereof were anti-CD3 antibodies and anti-CD28 antibodies, but the ratios of the antibodies were not provided). In particular, in the comparison group 1, the T cells were activated and/or expanded with a commercially available product TransAct™ T Cell reagent (Miltenyi Biotec), and in the comparison group 2, the T cells were activated and/or expanded with a commercially available product Dynabeads® Human T-Activator CD3/CD28 (ThermoFisher). In the experimental group, the T cell were activated and/or expanded with the knobby magnetic particles for which the surface was modified with the antibodies in which a ratio of anti-CD3 antibodies and anti-CD28 antibodies is 1:6, and the untreated initial cells of day 0 were served as a control group. The results are as shown in FIG. 7A to FIG. 7C.

Figure 7A:
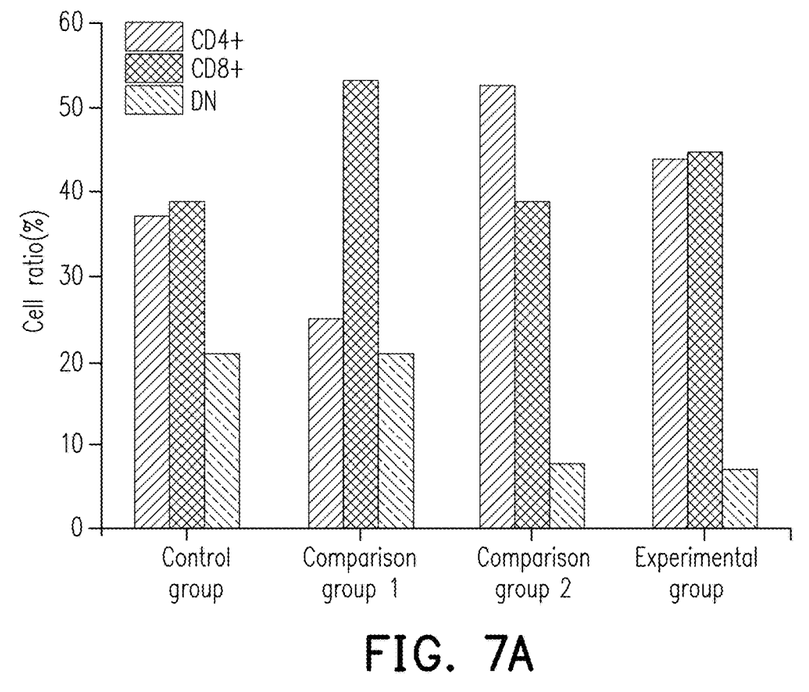
FIGS. 7A to 7C respectively show the analysis results for T cells using a flow cytometer, in which the comparison group 1, the comparison group 2, and the experimental group are T cells after T cell activation and/or expansion using commercial products TransAct™ T Cell reagent, Dynabeads® Human T-Activator CD3/CD28, and the aforementioned knobby magnetic particles having a surface modified with antibodies in which a ratio of the anti-CD3 antibody to the anti-CD28 antibody is 1:6, respectively. The untreated initial cells on day 0 were served as a control group. In particular, the horizontal axis illustrates each group, the left vertical axis represents the ratio of various cells in all cells (%), DN represents double negative T cells, Naive represents initial T cells, TCM represents central memory T cells, TEM represents effector memory T cells, and TEMRA represents T effector memory re-expressing CD45RA cells.
Figure 7B:
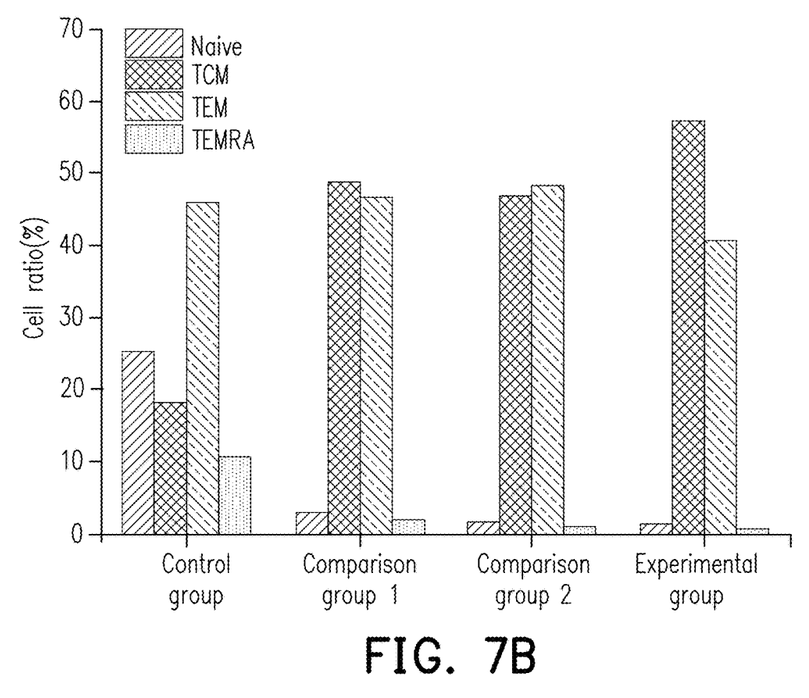
Figure 7C:
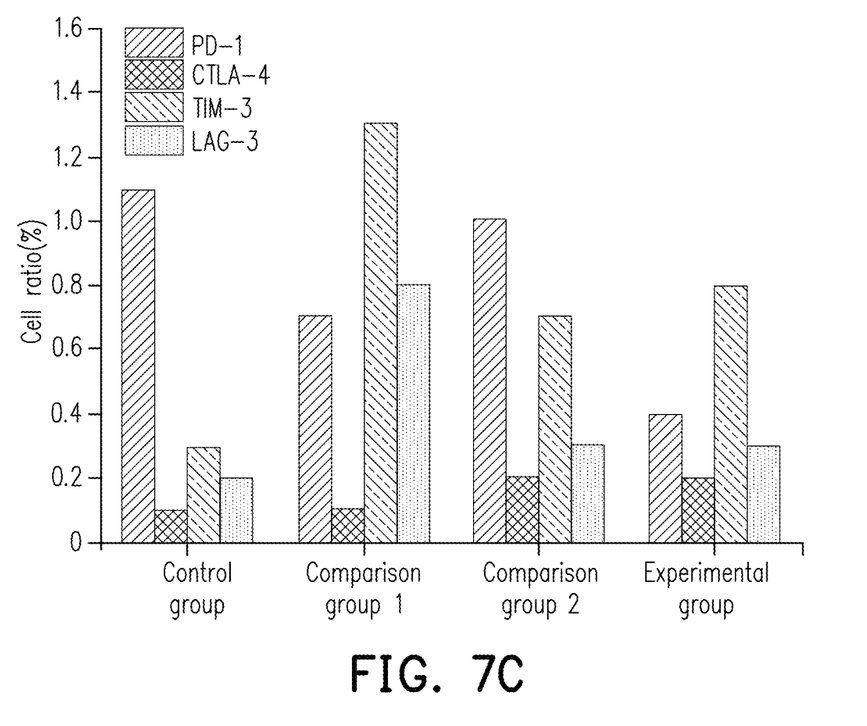

According to FIGS. 7A to 7C, it can be known that, compared to the comparison group 1 (TransAct™) and the comparison group 2 (Dynabeads®), the T cells of the experimental group (i.e., T cells activated and/or expanded by the surface-modified knobby magnetic particles of the disclosure) have the following characteristics: (1) the ratio of $CD4^+T$ cells to $CD8^+T$ cells is closest to 1:1 (FIG. 7A); (2) central memory T cells (TCM) occupy a higher ratio than effector memory T cells (TEM) (FIG. 7B); and (3) the sum of the ratios of T cells that expressed four different immunosuppressive molecules (PD-1 (programmed cell death-1), CTLA-4 (cytotoxic T-lymphocyte-associated antigen 4), TIM-3 (T-cell immunoglobulin and mucin-domain containing-3), and LAG-3 (lymphocyte-activation gene 3)) is minimum (FIG. 7C).

Based on the above, the magnetic particles of the disclosure have multi-protrusive surface similar to the most potent antigen-presenting cells in the human body, even similar to dendritic cells. Therefore, under the concept of biomimetics, it can be speculated that the knobby magnetic particles may be in contact with the immune cells in larger surface area, thereby contributing to the efficiency of activating immune cells and/or expanding the number of immune cells.

In addition, a specific type of immuno-inducing substance may be designed and modified on the surface of the magnetic particles of an embodiment of the disclosure such that the magnetic particles may be applied for the activation and expansion of γδ T cells to overcome the current issue of a lack of the related products applicable to γδ T cells. For example, in an embodiment, a peripheral blood mononuclear cell (PBMC) separated from whole blood is used as a source, and the knobby magnetic particles modified with the immuno-inducing substances may enhance the expansion ratio of γδ T cells by about 1.2 to 3.5 compared with magnetic particle-free conditions. Furthermore, since the magnetic particles have magnetic properties and specific immuno-inducing substances, they have the advantage of being able to rapidly separate and induce immune response, and thus, the immune cells may be applied to the research and development of techniques such as cancer immunotherapy.

It will be apparent to those skilled in the art that various modifications and variations may be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A method for in vitro activation and/or expansion of immune cells, comprising:
   a) providing magnetic particles, wherein surfaces of each of the magnetic particles are multi-protrusive and modified with at least one type of immuno-inducing substance, and wherein each of the magnetic particles comprises a copolymer core, a polymer layer, a magnetic substance layer, and a silicon-based layer from the inside to the outside;
   b) providing a cell solution, wherein the cell solution comprises at least one type of immune cell; and
   c) bringing the magnetic particles in contact with the cell solution such that the at least one type of immuno-inducing substance on the surface of each of the magnetic particles activates and/or expands the at least one type of immune cell in the cell solution, wherein surfaces of the copolymer core comprise a plurality of protrusions which are irregularly shaped, and the average height of the plurality of protrusions that is the average value of a vertical distance of a top side of each protrusion to a connection line between two bottom sides of each protrusion is 300 nm to 1000 nm.

2. The method for in vitro activation and/or expansion of immune cells of claim 1, wherein the average diameter of each of the magnetic particles is 1 μm to 50 μm.

3. The method for in vitro activation and/or expansion of immune cells of claim 1, wherein the at least one type of immune cell comprises a T cell, a NK cell, or a combination thereof.

4. The method for in vitro activation and/or expansion of immune cells of claim 3, wherein the at least one type of immune cell comprises a regulatory T cell.

5. The method for in vitro activation and/or expansion of immune cells of claim 4, wherein the at least one type of immune cell comprises an αβ T cell, a γδ T cell, or a combination thereof.

6. The method for in vitro activation and/or expansion of immune cells of claim 1, wherein the at least one type of immune cell comprises a γδ T cell.

7. The method for in vitro activation and/or expansion of immune cells of claim 1, wherein the at least one type of immuno-inducing substance comprises an anti-CD3 antibody and an anti-CD28 antibody.

8. The method for in vitro activation and/or expansion of the immune cells of claim 1, wherein the surface of each of the magnetic particles is modified with the at least one type of immuno-inducing substance through non-covalent binding, covalent binding, avidin-biotin interaction, electrostatic adsorption, hydrophobic adsorption, or a combination thereof.

9. The method for in vitro activation and/or expansion of immune cells of claim 1, wherein the copolymer core comprises a copolymer obtained by copolymerizing a monofunctional monomer and a bifunctional monomer.

10. The method for in vitro activation and/or expansion of immune cells of claim 9, wherein the volume percentage of the bifunctional monomer relative to the monofunctional monomer is 0.4% to 2%.

11. The method for in vitro activating and/or expansion of immune cells of claim 1, wherein the copolymer core comprises a styrene/divinylbenzene copolymer, a methyl methacrylate/triethylene glycol dimethacrylate copolymer, a methyl methacrylate/ethylene glycol dimethacrylate copolymer, a styrene/triethylene glycol dimethacrylate copolymer, a styrene/ethylene glycol dimethacrylate copolymer, or a methyl methacrylate/divinylbenzene copolymer.

12. The method for in vitro activation and/or expansion of immune cells of claim 1, wherein the polymer layer comprises at least one charged functional group.

13. The method for in vitro activation and/or expansion of immune cells of claim 12, wherein the at least one charged functional group comprises a carboxyl group, an amine group, or a combination thereof.

14. The method for in vitro activation and/or expansion of immune cells of claim 1, wherein the magnetic substance layer comprises a paramagnetic substance, a superparamagnetic substance, a ferromagnetic substance, a ferrite magnetic substance, or a combination thereof.

15. The method for in vitro activation and/or expansion of immune cells of claim 1, wherein the magnetic substance layer comprises an iron ion (Fe2+), a cobalt ion (Co2+), a nickel ion (Ni2+), or a combination thereof.

16. The method for in vitro activation and/or expansion of immune cells of claim 1, wherein a thickness of the silicon-based layer is at least 1 nm to 50 nm.

* * * * *